(12) United States Patent
Leonard et al.

(10) Patent No.: US 6,548,084 B2
(45) Date of Patent: *Apr. 15, 2003

(54) CONTROLLED RELEASE COMPOSITIONS

(75) Inventors: Graham Stanley Leonard, St Albans; David Philip Elder, Hertford, both of (GB)

(73) Assignee: SmithKline Beecham plc (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/391,796

(22) Filed: Sep. 9, 1999

(65) Prior Publication Data

US 2002/0028242 A1 Mar. 7, 2002

Related U.S. Application Data

(63) Continuation of application No. 08/817,911, filed as application No. PCT/EP96/03252 on Jul. 19, 1996, now abandoned.

(30) Foreign Application Priority Data

Jul. 20, 1995 (GB) .............................. 9514842

(51) Int. Cl.[7] ................... A61K 31/445; A61K 31/135; A61K 47/48
(52) U.S. Cl. ...................... 424/482; 424/464; 424/468; 424/470; 424/474; 424/476; 424/484; 424/486; 514/646; 514/647; 514/321
(58) Field of Search ................. 424/463, 464, 424/470, 474, 476, 482, 468, 484, 486; 514/646, 647, 321

(56) References Cited

U.S. PATENT DOCUMENTS 4,839,177 A    6/1989  Colombo et al.
4,847,092 A  * 7/1989  Thakkar et al.
5,102,666 A  * 4/1992  Acharya
5,422,123 A  * 6/1995  Conte et al.

FOREIGN PATENT DOCUMENTS

| EP | 0 269 303   | 11/1987 |             |
|----|-------------|---------|-------------|
| EP | A0 432 607  | 6/1991  |             |
| WO | WOA92 03124 | 3/1992  |             |
| WO | 92-09281    | * 6/1992 | ......... A61K/31/445 |
| WO | 95/15155    | * 6/1995 |             |
| WO | WOA95 15155 | 6/1995  |             |

OTHER PUBLICATIONS

Remington's Pharmaceutical Sciences 18th Edition, Mack Publishing Company (1990), Cover and pp. 1676 to 1686 of Chapter 91.

Remington's Pharmaceutical Sciences, 19th Edition, Mack Publishing Company (1995), Cover and pp. 1660, 1662, 1664 and 1665 of Chapter 94.

Chemical Abstracts, vol. 124, No. 10, Mar. 4, 1996, Columbus, Ohio, US; Abstract No. 127144, XP002018196, see abstract & CA,A,2 143 070 (P.MODI) Aug. 23, 1995.

Rickels et al., "Clinical Overview of Serotonin Reuptake Inhibitors", *J. Clin Psychiarty*, 51,12 suppl B (1990).

Paul Willner, "Antidepressants and serotonergic neurotransmission: An integrative review", Psychopharmacology, 85, pp. 387–404 (1985).

Drug Facts and Compounds, p. 1325 (1994 ed.).*

* cited by examiner

Primary Examiner—Thurman K. Page
Assistant Examiner—Humera N. Sheikh
(74) Attorney, Agent, or Firm—Wayne J. Dustman

(57) ABSTRACT

A controlled release or delayed release formulation contains a selective serotonin reuptake inhibitor (SSRI) such as paroxetine.

11 Claims, No Drawings

CONTROLLED RELEASE COMPOSITIONS

This application is a continuation of U.S. application Ser. No. 08/817,911 filed Aug. 26, 1997, now abandoned, which is a 371 of PCT/EP96/03252, filed Jul. 19, 1996.

The present invention relates to a novel formulation containing paroxetine or a pharmaceutically acceptable salt thereof, and to its use in the treatment and/or prophylaxis of certain disorders.

U.S. Pat. No. 4,007,196 describes inter alia a compound which is commonly known as paroxetine. This compound is a Selective Serotonin Reuptake Inhibitor (SSRI) and is currently marketed world-wide for the treatment and/or prophylaxis of depression.

The current formulation which is the only marketed formulation of paroxetine hydrochloride is a swallow tablet.

It has now been surprisingly found that controlled release and delayed release formulations containing paroxetine give rise to an unexpected reduction in the side effects associated with swallow tablets.

Accordingly, the present invention provides a controlled release or delayed release formulation containing paroxetine or a pharmaceutically acceptable salt thereof.

A further aspect of the invention provides a controlled release or delayed release formulation containing an SSRI. Examples of SSRIs other than paroxetine include fluoxetine (U.S. Pat. No. 4,314,081), fluvoxamine (U.S. Pat. No. 4,085,225), and sertraline (U.S. Pat. No. 4,536,518).

By controlled release is meant any formulation technique wherein release of the active substance from the dosage from is modified to occur at a slower rater than that from an immediate release product, such as a conventional swallow tablet or capsule.

By delayed release is meant any formulation technique wherein release of the active substance from the dosage form is modified to occur at a later time than that from a conventional immediate release product The subsequent release of active substance from a delayed release formulation may also be controlled as defined above.

Examples of controlled release formulations which are suitable for incorporating paroxetine and other SSRIs are described in:

Sustained Release Medications, Chemical Technology Review No. 177. Ed. J. C. Johnson. Noyes Data Corporation 1980.

Controlled Drug Delivery, Fundamentals and Applications, 2nd Edition. Eds. J. R. Robinson, V. H. L. Lee. Mercel Dekkes Inc. New York 1987.

Examples of delayed release formulations which are suitable for incorporating paroxetine and other SSRIs are described in:

Remington's Pharmaceutical Sciences 16th Edition, Mack Publishing Company 1980, Ed. A. Osol.

Such controlled release formulations are preferably formulated in a manner such that release of active substance such as paroxetine is effected predominantly during the passage through the stomach and the small intestine, and delayed release formulations are preferably formulated such that release of active substance such as paroxetine is avoided in the stomach and is effected predominantly during passage through the small intestine.

Said formulations are preferably formulated such that the release of the active substance is predominantly 1½ to 3 hours post ingestion.

The small intestine is suitably the duodenum, the ileum or the jejunem.

Patients who benefit most from the formulations of the present invention are those who are known to suffer from nausea upon oral administration using swallow tablets.

Preferred formulations are ultimately enteric coated tablets or caplets, wax or polymer coated tablets or caplets or time-release matrices, or combinations thereof.

Particularly preferred formulations are described in U.S. Pat. No. 5,102,666.

Thus, a particular aspect of the invention provides a polymeric controlled release composition comprising a reaction complex formed by the interaction of (1) a calcium polycarbophil component which is a water-swellable, but water insoluble, fibrous cross-linked carboxy-functional polymer, said polymer containing (a) a plurality of repeating units of which at least about 80% contain at least one carboxyl functionality, and (b) about 0.05 to about 1.5% cross-linking agent substantially free from polyalkenyl polyether, said percentages being based upon the weights of unpolymerised repeating unit and cross-linking agent, respectively, with (2) water, in the presence of an active agent selected from the group consisting of SSRIs such as paroxetine. The amount of calcium polycarbophil present is from about 0.1 to about 99% by weight, for example about 10%. The amount of active agent present is from about 0.0001 to about 65% by weight, for example between about 5 and 20%. The amount of water present is from about 5 to about 200% by weight, for example between about 5 and 10%. The interaction is carried out at a pH of between about 3 and about 10, for example about 6 to 7. The calcium polycarbophil is originally present in the form of a calcium salt containing from about 5 to about 25% calcium.

Further particularly preferred formulations are described in U.S. Pat. No. 5,422,123.

Thus, a further particular aspect of the invention provides a system for the controlled release of an active substance which is an SSRI such as paroxetine, comprising (a) a deposit-core comprising an effective amount of the active substance and having defined geometric form, and (b) a support-plafform applied to said deposit-core, wherein said deposit-core contains at least the active substance, and at least one member selected from the group consisting of (1) a polymeric material which swells on contact with water or aqueous liquids and a gellable polymeric material wherein the ratio of the said swellable polymeric material to said gellable polymeric material is in the range 1:9 to 9:1, and (2) a single polymeric material having both swelling and gelling properties, and wherein the support-platform is an elastic support, applied to said deposit-core so that it partially covers the surface of the deposit-core and follows changes due to hydration of the deposit-core and is slowly soluble and/or slowly gellable in aqueous fluids. The support-platform may comprise polymers such as hydroxypropylmethylcellulose, plasticizers such as a glyceride, binders such as polyvinylpyrrolidone, hydrophilic agents such as lactose and silica, and/or hydrophobic agents such as magnesium stearate and glycerides. The polymer(s) typically make up 30 to 90% by weight of the support-platform, for example about 35 to 40%. Plasticizer may make up at least 2% by weight of the support-platform, for example about 15 to 20%. Binder(s), hydrophilic agent(s) and hydrophobic agent(s) typically total up to about 50% by weight of the support-platform, for example about 40 to 50%.

Paroxetine used in the present invention is suitably in the form of the free base or a pharmaceutically acceptable salt form thereof. Preferably, paroxetine is suitably in the form of the hydrochloride hemihydrate.

Paroxetine hydrochloride hemihydrate may be prepared according to the procedures generally outlined in U.S. Pat. No. 4,721,723.

Paroxetine in the form of a controlled release or delayed release formulation can be used to treat and prevent the following disorders:

Alcoholism

Anxiety

Depression

Obsessive Compulsive Disorder

Panic Disorder

Chronic Pain

Obesity

Senile Dementia

Migraine

Bulimia

Anorexia

Social Phobia

Pre-Menstrual Syndrome (PMS)

Adolescent Depression

Trichotillomania

Dysthymia

Substance Abuse

These disorders are herein after referred to as "the disorders".

The present invention provides a method of treating and/or preventing the disorders by administering an effective and/or a prophylactic amount of a controlled release or delayed release formulation containing paroxetine or a pharmaceutically acceptable salt thereof, to a sufferer in need thereof.

The present invention further provides the use of a controlled release or delayed release formulation containing paroxetine or a pharmaceutically acceptable salt thereof in the manufacture of a medicament, for treating and/or preventing the disorders.

The present invention also provides a pharmaceutical composition for use in the treatment and/or prevention of the disorders which comprises a controlled release or delayed release formulation containing paroxetine or a pharmaceutically acceptable salt thereof.

The following examples illustrate the present invention.

EXAMPLE 1

(Hydrophilic Matrix)

|  | % w/w |
|---|---|
| Intragranular | |
| Paroxetine Hydrochloride | 11.45 |
| Methocel E5 | 1.25 |
| Lactose | 12.3 |
| Extragranular | |
| Methocel K100LV | 30.0 |
| Lactose | 44.0 |
| Magnesium Stearate | 1.0 |
| TOTAL | 100.0 |

EXAMPLE 2

(Hydrophilic Matrix)

|  | % w/w |
|---|---|
| Intragranular | |
| Paroxetine Hydrochloride | 11.45 |
| Methocel E5 | 1.25 |
| Lactose | 12.3 |
| Extragranular | |
| Methocel K100LV | 27.5 |
| Methocel K4M | 7.5 |
| Lactose | 39.0 |
| Magnesium Stearate | 1.0 |
| TOTAL | 100.0 |

EXAMPLE 3

(pH Sensitive Coat on Immediate Release Core)

|  | % w/w |
|---|---|
| Tablet Core | |
| Paroxetine Hydrochloride | 11.45 |
| Lactose | 64.05 |
| Microcrystalline Cellulose | 20.0 |
| Sodium Starch Glycollate | 4.0 |
| Magnesium Stearate | 0.5 |
| TOTAL | 100.0 |
| Tablet Coating (apply approximately 6–10% of tablet core weight) | |
| Hydroxypropylmethylcellulose Phthalate | 90.0 |
| Triacetin | 10.0 |

EXAMPLE 4

(pH Sensitive Coat on Immediate Release Core)

Tablet Core as in Example 3

| Tablet Coating (apply approximately 6–10% of tablet core weight) | % w/w |
|---|---|
| Cellulose Acetate Phthalate | 90.0 |
| Diethyl Phthalate | 10.0 |

EXAMPLE 5

(Controlled Release Coating on Immediate Release Core)

Tablet Core as in Example 3

| Tablet Coating (apply approximately 5–12% of tablet core weight) | % w/w |
|---|---|
| Eudragit RS 100 | 86.0 |
| Dibutyl Phthalate | 10.0 |
| Talc | 4.0 |
| FD&C Yellow No. 6 | 0.01 |

EXAMPLE 6

(pH Sensitive Coat on Controlled Release Core.)

Tablet Core as in Example 3
Tablet Coating as in Example 3

EXAMPLE 7

(Encapsulated Controlled Release Coated Beads)

| Pellet | % w/w (approx) |
|---|---|
| Non Pareil Seed | 30 |
| Paroxetine Hydrochloride | 40 |
| Gelatin | 8 |
| Lactose | 20 |
| Talc | 2 |
| Coating | % w/w |
| Glycerylmonostearate | 36.6 |
| Glyceryldistearate | 53.4 |
| White Wax | 10.0 |

EXAMPLE 8

(Controlled Release Bilayer Tablet)

| Component | mg/tablet | Function |
|---|---|---|
| Active Layer | | |
| Paroxetine Hydrochloride | 22.89* | Active |
| Methocel K4M | 15.00 | Hydrogel polymer |
| Lactose monohydrate | 62.0 | Hydrophilic agent |
| Polyvinylpyrrolidone | 3.0 | Binder |
| Magnesium stearate | 1.0 | Hydrophobic agent |
| Syloid 244 | 1.0 | Hydrophilic agent |
| Support platform | | |
| Compritol 888 | 15.04 | Plasticizer |
| Lactose monohydrate | 29.32 | Hydrophilic agent |
| Polyvinylpyrrolidone | 4.0 | Binder |
| Magnesium stearate | 1.52 | Hydrophobic agent |
| Methocel E5 | 29.32 | Hydrogel polymer |
| Iron oxide | 0.08 | Colourant |
| Total tablet weight | 184.89 mg | |

*Equivalent to 20 mg paroxetine as free base.

The powder blend for each layer was wet granulated in a high shear mixer/granulator and dried in a fluid bed drier. The bilayer tablets were compressed on a Manesty triple layer press.

EXAMPLE 9

(Enteric Coated Calcium Polycarbophil Formulation)

| Component | mg/tablet | Function |
|---|---|---|
| Core | | |
| Paroxetine Hydrochloride | 22.89* | Active |
| Calcium polycarbophil | 20.00 | Matrix |
| Lactose anhydrous | 146.11 | Hydrophilic agent/diluent |
| Polyvinylpyrrolidone | 10.0 | Binder |
| Magnesium stearate | 1.0 | Hydrophobic agent/lubricant |
| Water** | 0.024 | Granulating liquid |
| Enteric coat | | |
| Eudragit | 22.19 | Polymer |
| Talc | 1.53 | Lubricant |
| Triethyl citrate | 1.00 | Plasticizer |
| Water** | 24.6 | Diluent |
| Film coat | | |
| Opadry pink | 10.5 | Film coat |
| Water** | 94.5 | Diluent |
| Polish coat | | |
| Opadry clear | 0.750 | |
| Water** | 29.3 | Diluent |

*Equivalent to 20 mg paroxetine as free base.
**Removed during processing.

The core constituents were wet granulated in a high shear mixer/granulator, and dried in a fluid bed drier. The magnesium stearate was then added and the mixture processed in a low shear mixer. The mix was then compressed on a B type rotary tablet press. Coating was carried out using an Accela cota.

EXAMPLE 10

(Controlled Release Bilayer Tablet)

| Component | mg/tablet | Function |
|---|---|---|
| Active Layer | | |
| Paroxetine Hydrochloride | 22.89* | Active |
| Methocel K4M | 20.00 | Hydrogel polymer |
| Lactose monohydrate | 60.0 | Hydrophilic agent |
| Polyvinylpyrrolidone | 5.0 | Binder |
| Magnesium stearate | 1.0 | Hydrophobic agent |
| Syloid 244 | 1.0 | Hydrophilic agent |
| Support platform | | |
| Compritol 888 | 14.72 | Plasticizer |
| Lactose monohydrate | 30.60 | Hydrophilic agent |
| Polyvinylpyrrolidone | 2.80 | Binder |
| Magnesium stearate | 0.80 | Hydrophobic agent |
| Methocel E5 | 30.60 | Hydrogel polymer |
| Syloid 244 | 0.40 | Hydrophilic agent |
| Iron oxide | 0.08 | Colourant |
| Total tablet weight | 189.89 mg | |

*Equivalent to 20 mg paroxetine as free base.

The process was as described in Example 8.

EXAMPLE 11

(Controlled Release Bilayer Tablet)

| Component | mg/tablet | Function |
|---|---|---|
| Active Layer | | |
| Paroxetine Hydrochloride | 22.89* | Active |
| Methocel K4M | 15.00 | Hydrogel polymer |
| Lactose monohydrate | 63.31 | Hydrophilic agent |
| Polyvinylpyrrolidone | 2.0 | Binder |

-continued

| Component | mg/tablet | Function |
|---|---|---|
| Magnesium stearate | 1.0 | Hydrophobic agent |
| Syloid 244 | 0.40 | Hydrophilic agent |

Support platform - as in Example 10.

| Total tablet weight | 184.60mg |
|---|---|

*Equivalent to 20 mg paroxetine as free base.

The process was as described in Example 8.

EXAMPLE 12
(Enteric Coated Controlled Release Bilayer Tablet)

| Component | mg/tablet | Function |
|---|---|---|
| Active Layer | | |
| Paroxetine Hydrochloride | 28.61* | Active |
| Methocel K4M | 18.75 | Hydrogel polymer |
| Lactose monohydrate | 79.14 | Hydrophilic agent |
| Polyvinylpyrrolidone | 2.50 | Binder |
| Magnesium stearate | 1.25 | Hydrophobic agent |
| Syloid 244 | 0.50 | Hydrophilic agent |
| Support platform | | |
| Compritol 888 | 15.04 | Plasticizer |
| Lactose monohydrate | 30.50 | Hydrophilic agent |
| Polyvinylpyrrolidone | 4.00 | Binder |
| Magnesium stearate | 0.80 | Hydrophobic agent |
| Methocel E5 | 29.32 | Hydrogel polymer |
| Syloid 244 | 0.32 | Hydrophilic agent |
| Iron oxide | 0.02 | Colourant |
| Enteric coating | | |
| Eudragit | 13.27 | Polymer |
| Talc | 3.31 | Lubricant |
| Triethyl citrate | 1.33 | Plasticizer |
| Water** | 36.25 | Diluent |
| Total tablet weight | 228.66 mg | |

*Equivalent to 25 mg paroxetine as free base.
**Removed during processing.

The process was as described in Example 9.

EXAMPLE 3
GI Tolerance Study

The design of the study is outlined below

Subjects: Normal healthy volunteers

Design: Parallel group, placebo controlled, double blind

Treatment: (a) Placebo, (b) Immediate release paroxetine, (c) Example 8 formulation, (d) Example 8 formulation with enteric coating.

Dosage: 30 mg once daily for 3 days

Number of subjects: 452 evaluable (488 randomised, 485 evaluable)

The study was conducted to compare the incidence, severity and duration of nausea and vomiting, and diarrhoea (theoretically if the controlled release formulations slow down absorption of paroxetine then, as paroxetine is known to be prokinetic to the GI tract there may be an increased incidence).

Adverse experiences (AE) information was assessed each morning at the time of dosing and again 24 hours following the last dose. Investigators and subjects were given diary cards detailing how to classify severity of AEs in order to standardise as much as possible across all 6 centres.

Of the 485 evaluable subjects, 18 (3.7%) withdrew, 17 because of adverse events. Subjects with nausea/vomiting on the day of withdrawal were more common on (b) than either of (c) and (d).

The incidence of nausea/vomiting and diarrhoea is shown in the table below:

| | (b) | (c) | (d) | Placebo |
|---|---|---|---|---|
| Incidence of nausea | 59% | 49% | 39% | 13% |
| Incidence of diarrhoea | 15% | 21% | 20% | 7% |

The incidence of nausea was increased for both (b) and placebo compared to the expected rates of approximately 25% and 5% respectively for volunteers at these dosages for 3 days duration. The overall incidence of nausea was less on (c) and (d) than on (b). The severity of nausea was also decreased as shown in the next table.

| Nausea severity | (b) | (c) | (d) | Placebo |
|---|---|---|---|---|
| None | 50 (41%) | 63 (52%) | 74 (61%) | 104 (87%) |
| Mild | 45 (37%) | 40 (33%) | 30 (25%) | 16 (13%) |
| Moderate | 21 (17%) | 17 (14%) | 15 (12%) | 0 (0%) |
| Severe | 6 (5%) | 1 (1%) | 3 (2%) | 0 (0%) |

Severity of diarrhoea is reported in the table below.

| Severity of diarrhoea | (b) | (c) | (d) | Placebo |
|---|---|---|---|---|
| None | 104 (85%) | 95 (79%) | 97 (80%) | 112 (93%) |
| Mild | 16 (13%) | 16 (13%) | 16 (13%) | 8 (7%) |
| Moderate | 1 (1%) | 8 (7%) | 9 (7%) | 0 (0%) |
| Severe | 1 (1%) | 2 (2%) | 0 (0%) | 0 (0%) |

In conclusion, there appears to be a trend for (c) to reduce the incidence of nausea and the dropout rate due to adverse events in comparison to (b), but analysis of the results was complicated by a statistically significant treatment-by-centre difference. (d) shows a halving in the dropout rate and a fall in incidence of nausea of 20% (a proportional fall of 33%). In addition there is a reduction in severity of nausea of those individuals who report nausea on (c) and (d). There is an increase in incidence of diarrhoea on both of (c) and (d) in relation to (b), but this is confined to an increase in the number of individuals reporting moderate diarrhoea and there is no increase in those with severe diarrhoea

What is claimed is:

1. A method of reducing the incidence of nausea and vomiting associated with the administration of a selective serotonin reuptake inhibiting compound selected from fluvoxamine and sertraline, or a pharmaceutically acceptable salt thereof, which method consists of administering an effective amount of a selective serotonin reuptake inhibiting compound in a controlled release, delayed release or a combination of a controlled release and delayed release swallow pharmaceutical formulation that, upon oral administration, releases the selective serotonin reuptake inhibiting compound predominantly in the small intestine.

2. The method of claim 1 in which the formulation is an enteric coated controlled release bilayer tablet.

3. A method of reducing the incidence of nausea and vomiting associated with the administration of a selective serotonin reuptake inhibiting compound selected from paroxetine, fluoxetine, fluvoxamine and sertraline, or a pharmaceutically acceptable salt thereof, which method consists of administering an effective amount of the selective serotonin reuptake inhibiting compound as a polymeric controlled release composition comprising a reaction complex formed by the interaction of (1) a calcium polycarbophil component which is a water-swellable, but water insoluble, fibrous cross-linked carboxy-functional polymer, said polymer containing (a) a plurality of repeating units of which at least about 80% contain at least one carboxyl functionality, and (b) about 0.05 to about 1.5% cross-linking agent substantially free from polyalkenyl polyether, said percentages being based upon the weights of unpolymerized repeating unit and cross-linking agent, respectively with (2) water, in the presence of a selective serotonin reuptake inhibiting compound.

4. A method of reducing the incidence of nausea and vomiting associated with the administration of a selective serotonin reuptake inhibiting compound paroxetine, or a pharmaceutically acceptable salt thereof, which method consists of administering an effective amount of the selective serotonin reuptake inhibiting compound as a polymeric controlled release composition comprising a reaction complex formed by the interaction of (1) a calcium polycarbophil component which is a water-swellable, but water insoluble, fibrous cross-linked carboxy-functional polymer, said polymer containing (a) a plurality of repeating units of which at least about 80% contain at least one carboxyl functionality, and (b) about 0.05 to about 1.5% cross-linking agent substantially free from polyalkenyl polyether, said percentages being based upon the weights of unpolymerized repeating unit and cross-linking agent, respectively with (2) water, in the presence of a selective serotonin reuptake inhibiting compound.

5. A method of reducing the incidence of nausea and vomiting associated with the administration of a selective serotonin reuptake inhibiting compound which method consists of administering an effective amount of a selective serotonin reuptake inhibiting compound in a controlled release, delayed release or a combination of a controlled release and delayed release swallow pharmaceutical formulation that, upon oral administration, releases the selective serotonin reuptake inhibiting compound predominantly in the small intestine, said formulation comprising (a) a deposit-core comprising an effective amount of a selective serotonin reuptake inhibiting compound and having defined geometric form, and (b) a support-platform applied to said deposit-core, wherein said deposit-core contains at least the active substance, and at least one member selected from the group consisting of (1) a polymeric material which swells on contact with water or aqueous liquids and a gellable polymeric material wherein the ratio of the said swellable polymeric material to said gellable polymeric materials in the range 1:9 to 9:1, and (2) a single polymeric material having both swelling and gelling properties, and wherein the support-platform is an elastic support, applied to said deposit-core so that it partially covers the surface of the deposit-core and follows changes due to hydration of the deposit-core and is slowly soluble and/or slowly gellable in aqueous fluids.

6. A method of reducing the incidence of nausea and vomiting associated with the administration of a selective serotonin reuptake inhibiting compound paroxetine or a pharmaceutically acceptable salt thereof, which method consists of administering an effective amount of a selective serotonin reuptake inhibiting compound in a controlled release, delayed release or a combination of a controlled release and delayed release swallow pharmaceutical formulation that, upon oral administration, releases the selective serotonin reuptake inhibiting compound predominantly in the small intestine, said formulation comprising (a) a deposit-core comprising an effective amount of the selective serotonin reuptake inhibiting compound and having defined geometric form, and (b) a support-platform applied to said deposit-core, wherein said deposit-core contains at least the active substance, and at least one member selected from the group consisting of (1) a polymeric material which swells on contact with water or aqueous liquids and a gellable polymeric material wherein the ratio of the said swellable polymeric material to said gellable polymeric materials in the range 1:9 to 9:1, and (2) a single polymeric material having both swelling and gelling properties, and wherein the support-platform is an elastic support, applied to said deposit-core so that it partially covers the surface of the deposit-core and follows changes due to hydration of the deposit-core and is slowly soluble and/or slowly gellable in aqueous fluids.

7. A controlled release, delayed release or a combination of a controlled release and delayed release swallow pharmaceutical formulation that reduces the incidence of nausea and vomiting associated with the administration of a selective serotonin reuptake inhibiting compound that, upon oral administration, releases the selective serotonin reuptake inhibiting compound predominantly in the small intestine, which formulation is a polymeric composition comprising a reaction complex formed by the interaction of (1) a calcium polycarbophil component which is a water-swellable, but water insoluble, fibrous cross-linked carboxy-functional polymer, said polymer containing (a) a plurality of repeating units of which at least about 80% contain at least one carboxyl functionality, and (b) about 0.05 to about 1.5% cross-linking agent substantially free from polyalkenyl polyether, said percentages being based upon the weights of unpolymerized repeating unit and cross-linking agent, respectively with (2) water, in the presence of a selective serotonin reuptake inhibiting compound.

8. A controlled release, delayed release or a combination of a controlled release and delayed release swallow pharmaceutical formulation that reduces the incidence of nausea and vomiting associated with the administration of the selective serotonin reuptake inhibiting compound paroxetine, or a pharmaceutically acceptable salt thereof that, upon oral administration, releases the selective serotonin reuptake inhibiting compound predominantly in the small intestine, which formulation is a polymeric composition comprising a reaction complex formed by the interaction of (1) a calcium polycarbophil component which is a water-swellable, but water insoluble, fibrous cross-linked carboxy-functional polymer, said polymer containing (a) a plurality of repeating units of which at least about 80% contain at least one carboxyl functionality, and (b) about 0.05 to about 1.5% cross-linking agent substantially free from polyalkenyl polyether, said percentages being based upon the weights of unpolymerized repeating unit and cross-linking agent, respectively with (2) water, in the presence of the selective serotonin reuptake inhibiting compound.

9. A controlled release, delayed release or a combination of a controlled release and delayed release swallow pharmaceutical formulation that reduces the incidence of nausea and vomiting associated with the administration of the selective serotonin reuptake inhibiting compound that, upon oral administration, releases the selective serotonin reuptake inhibiting compound predominantly in the small intestine, which formulation comprises (a) a deposit-core comprising an effective amount of the active substance and having defined geometric form, and (b) a support-platform applied to said deposit-core, wherein said deposit-core contains at least the active substance, and at least one member selected from the group consisting of (1) a polymeric material which swells on contact with water or aqueous liquids and a gellable polymeric material wherein the ratio of the said swellable polymeric material to said gellable polymeric materials in the range 1:9 to 9:1, and (2) a single polymeric material having both swelling and gelling properties, and wherein the support-platform is an elastic support, applied to said deposit-core so that it partially covers the surface of the deposit-core and follows changes due to hydration of the deposit-core and is slowly soluble and/or slowly gellable in aqueous fluids.

10. A controlled release, delayed release or a combination of a controlled release and delayed release swallow pharmaceutical formulation that reduces the incidence of nausea and vomiting associated with the administration of the selective serotonin reuptake inhibiting compound paroxetine, or a pharmaceutically acceptable salt thereof that, upon oral administration, releases the selective serotonin reuptake inhibiting compound predominantly in the small intestine, which formulation comprises (a) a deposit-core comprising an effective amount of the active substance and having defined geometric form, and (b) a support-platform applied to said deposit-core, wherein said deposit-core contains at least the active substance, and at least one member selected from the group consisting of (1) a polymeric material which swells on contact with water or aqueous liquids and a gellable polymeric material wherein the ratio of the said swellable polymeric material to said gellable polymeric materials in the range 1:9 to 9:1, and (2) a single polymeric material having both swelling and gelling properties, and wherein the support-platform is an elastic support, applied to said deposit-core so that it partially covers the surface of the deposit-core and follows changes due to hydration of the deposit-core and is slowly soluble and/or slowly gellable in aqueous fluids.

11. A process for preparing a controlled or delayed release formulation of a selective serotonin reuptake inhibiting compound, which comprises combining (1) a calcium polycarbophil component which is a water-swellable, but water insoluble, fibrous cross-linked carboxy-functional polymer, said polymer containing (a) a plurality of repeating units of which at least about 80% contain at least one carboxyl functionality, and (b) about 0.05 to about 1.5% cross-linking agent substantially free from polyalkenyl polyether, said percentages being based upon the weights of unpolymerised repeating unit and cross-linking agent, respectively, with (2) water, in the presence of a selective serotonin reuptake inhibiting compound.

* * * * *